(12) United States Patent
Ye et al.

(10) Patent No.: US 10,656,143 B2
(45) Date of Patent: May 19, 2020

(54) METHODS AND APPARATUSES FOR IDENTIFYING RED BLOOD CELLS INFECTED BY PLASMODIUM

(71) Applicant: Shenzhen Mindray Bio-Medical Electronics Co., Ltd., Shenzhen (CN)

(72) Inventors: Bo Ye, Shenzhen (CN); Cheng Qian, Shenzhen (CN); Huan Qi, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 618 days.

(21) Appl. No.: 14/355,544

(22) PCT Filed: Oct. 31, 2012

(86) PCT No.: PCT/CN2012/083864
§ 371 (c)(1),
(2) Date: May 21, 2014

(87) PCT Pub. No.: WO2013/064078
PCT Pub. Date: May 10, 2013

(65) Prior Publication Data
US 2014/0308697 A1    Oct. 16, 2014

(30) Foreign Application Priority Data
Oct. 31, 2011    (CN) .......................... 2011 1 0337707

(51) Int. Cl.
| | |
|---|---|
| *G01N 33/50* | (2006.01) |
| *G01N 33/569* | (2006.01) |
| *G01N 33/80* | (2006.01) |
| *G01N 21/64* | (2006.01) |
| *G01N 21/51* | (2006.01) |
| *G01N 21/49* | (2006.01) |
| *G01N 21/47* | (2006.01) |

(52) U.S. Cl.
CPC ......... *G01N 33/5091* (2013.01); *G01N 21/49* (2013.01); *G01N 21/51* (2013.01); *G01N 21/64* (2013.01); *G01N 33/56905* (2013.01); *G01N 33/80* (2013.01); *G01N 2021/4707* (2013.01); *G01N 2021/4711* (2013.01); *G01N 2021/4726* (2013.01); *G01N 2021/6493* (2013.01); *G01N 2333/445* (2013.01)

(58) Field of Classification Search
None
See application file for complete search history.

(56) References Cited

U.S. PATENT DOCUMENTS

| | | | |
|---|---|---|---|
| 2006/0223137 A1 | 10/2006 | Yoshida et al. | |
| 2007/0020721 A1* | 1/2007 | Yoshida | G01N 15/1459 435/34 |
| 2010/0104169 A1* | 4/2010 | Yamada | G01N 15/1429 382/134 |

FOREIGN PATENT DOCUMENTS

| | | |
|---|---|---|
| CN | 101389947 | 3/2009 |
| CN | 102016573 A | 4/2011 |
| CN | 102016577 A | 4/2011 |
| CN | 102109430 | 6/2011 |
| EP | 1746407 A2 | 1/2007 |
| WO | WO2009136570 A1 | 11/2009 |

OTHER PUBLICATIONS

Tilley, L. et al. 2007. Illuminating Plasmodium falciparum-infected red blood cells. Trends in Parasitology 23(6): 268-277. specif. p. 268.*
MedlinePlus Medical Dictionary. Plasmodium. Datasheet [online]. Merriam-Webster. [retrieved on Apr. 11, 2016]. Copyright 2016. Merriam-Webster, Inc. Retrieved from the Internet: <URL: http:// http://c.merriam-webster.com/medlineplus/plasmodium> p. 1.*
Reinders, P.P. et al. 1995. Computer software for testing drug susceptibility of malaria parasites. Cytometry 19:273-281. specif. pp. 273, 274, 275, 277.*
Kim, Y.R. et al. 2003. Automated red blood cell differential analysis on a multi-angle light scatter/fluorescence hematology analyzer. Cytometry PartB (Clinical Cytometry) 56B: 43-54. specif. pp. 43, 44.*
Saul, A. et al. 1982. Plasmodium falciparum: automated assay of erythrocyte invasion using flow cytofluorometry. Experimental Parasitology 54: 64-71. specif. pp. 64, 66, 67.*
Lehner, J. et al. 2007. Automation in hematology. Transfusion Medicine and Hemotherapy 34: 328-339. specif. pp. 331, 332, 333, 334.*
Fernando, N.T. 2011. Novel near-infrared cyanine dyes for fluorescence imaging in biological systems. Chemistry Dissertations. Dept. of Chemistry. Georgia State Univ. pp. 1-141; specif. pp. 3, 5.*

(Continued)

*Primary Examiner* — Thomas J. Visone
*Assistant Examiner* — Sharon M. Papciak
(74) *Attorney, Agent, or Firm* — Kory D. Christensen

(57) ABSTRACT

The present disclosure relates to the field of medical technology, which provides methods and apparatuses for identifying red blood cells infected by plasmodium. The methods may include: obtaining a forward-scattered light signal, a side-scattered light signal and an optional fluorescence signal from cells in a blood sample; obtaining a first two-dimensional scattergram according to the forward-scattered light signal and the side-scattered light signal, or obtaining a three-dimensional scattergram according to the forward-scattered light signal, the side-scattered light signal and the fluorescence signal; and identifying cells located in a predetermined area of the first two-dimensional scattergram or the three-dimensional scattergram as the red blood cells infected by plasmodium. The apparatuses perform the methods. The methods and apparatuses can have better identification accuracy.

3 Claims, 5 Drawing Sheets

(56) References Cited

OTHER PUBLICATIONS

Campuzano-Zuluaga et al., "Design of Malaria Diagnostic Criteria for the Sysmex XE-2100 Hematology Analyzer", American Journal of Tropical Medicine & Hygiene, 2010, pp. 402-411.

\* cited by examiner

METHODS AND APPARATUSES FOR IDENTIFYING RED BLOOD CELLS INFECTED BY PLASMODIUM

RELATED APPLICATION

This application claims priority to Chinese Patent Application No. 201110337707.8, filed on Oct. 31, 2011, the disclosure of which is fully incorporated herein by reference.

TECHNICAL FIELD

The present disclosure relates to the field of medical technology, more particularly to techniques for identifying red blood cells (RBCs) infected by plasmodium.

BRIEF SUMMARY

The present disclosure relates to methods and apparatuses for blood analysis. More particularly, the present disclosure relates to method for identifying red cells infected by plasmodium and apparatuses of using the methods to analyze blood samples.

In one aspect of the present disclosure, a method for identifying red blood cells infected by plasmodium can include:
obtaining a forward-scattered light signal, a side-scattered light signal and an optional fluorescence signal from cells in a blood sample;
obtaining a first two-dimensional scattergram according to the forward-scattered light signal and the side-scattered light signal, or obtaining a three-dimensional scattergram according to the forward-scattered light signal, the side-scattered light signal and the fluorescence signal; and
identifying cells located in a predetermined area of the first two-dimensional scattergram or the three-dimensional scattergram as the red blood cells infected by plasmodium.

In another aspect of the present disclosure, an apparatus for identifying red blood cells infected by plasmodium can include:
a signal acquisition unit, which obtains a forward-scattered light signal, a side-scattered light signal and an optional fluorescence signal from cells in a blood sample;
a diagram generation unit, which obtains a first two-dimensional scattergram according to the forward-scattered light signal and the side-scattered light signal, or obtains a three-dimensional scattergram according to the forward-scattered light signal, the side-scattered light signal and the fluorescence signal; and
an identification unit, which identifies cells located in a predetermined area of the first two-dimensional scattergram or the three-dimensional scattergram as the red blood cells infected by plasmodium.

In still another aspect of the present disclosure, a method for identifying red blood cells infected by plasmodium can include:
treating a blood sample with a reagent;
passing the treated sample through a detection area of a flow cytometer;
obtaining a forward-scattered light intensity, a side-scattered light intensity and an optional fluorescence intensity of cells in the blood sample;
obtaining a first scattergram of the blood sample, which is a two-dimensional scattergram or a three-dimensional scattergram; and
identifying cells located in a predetermined area of the first scattergram as the red blood cells infected by plasmodium.

In yet another aspect of the present disclosure, an apparatus for identifying red blood cells infected by plasmodium that can include:
a blood treatment unit, which treats a blood sample;
a detection unit, which detects the treated blood sample and obtains scattered light signals; and
a data processing unit, which obtains a scattergram according to the scattered light signals, and identifies cells located in a predetermined area of the scattergram as the red blood cells infected by plasmodium.

A blood sample can be treated by a reagent, and then detected by a flow cytometer to obtain a scattergram. Red blood cells infected by plasmodium can be identified according to cell areas of the scattergram. The methods described herein may be performed using an automatic analyzer, so people's influence can be reduced and the method might have better identification accuracy. So the methods and apparatuses described herein may have faster detection speed and higher identification accuracy. Moreover, since all cells in a blood sample can be analyzed with these methods and the number of detected cells can be high, missed diagnosis caused by an insufficient number of blood cells in the inspection area would likely not occur, thereby further improving the identification accuracy.

It is noted that in FIG. 1, FIG. 2, FIG. 8, FIG. 9 and FIG. 10 each black dot represents one cell, and each ellipse represents one cell-type area.

DETAILED DESCRIPTION

Plasmodium infection is a commonly encountered infectious disease in many areas of the world, especially in Africa. Plasmodium might enter human blood circulation system after mosquito bite, which can reproduce and proliferate in red blood cells. Malaria has such clinical symptoms as fever and cool, and might cause people to die if the disease cannot be cured in time. Malaria is an infectious disease that threatens people health.

Malaria diagnosis needs patient's medical history, travel history, clinical symptoms and microscopic examination. Identification of red blood cells infected by plasmodium is important to malaria diagnosis. Conventional identification method is to check cell morphology under a microscope. In this cell morphology examination, a blob of blood sample was smeared on a slide. Missed diagnosis might occur if an insufficient number of cells were examined. In addition, because examiners may have different capabilities, the accuracy and efficiency of the conventional method may not be satisfied.

The present disclosure provides methods for identifying red blood cells infected by plasmodium that can be more accurate and efficient.

The following embodiments illustrate various features of the present invention but are not intended in any way to limit the scope of the invention as set forth in the claims.

In order to screen blood samples infected by plasmodium, there is a need to develop a new automatic method for identifying blood cells infected by plasmodium.

After studying malaria patients' blood samples, it has been found that there may be difference in cytomembrane feature and inter-cellular morphology between normal red blood cells and those infected by plasmodium. Red blood cells infected by plasmodium can have some features similar to normal white blood cells, so it may be possible to identify red blood cells infected by plasmodium if white blood cells are classified. Specifically, it has been found that red blood cells infected by plasmodium can have smaller cell size and more complex inter-cellular morphology than normal white blood cells, so it may be possible for red blood cells infected by plasmodium to appear in the lower right portion of the normal white blood cells area in a scattergram classifying white blood cells (X-axis is side-scattered light intensity, Y-axis is forward-scattered light intensity). After many experiments where scattered light signals from blood samples were processed and analyzed, it has been found that a cell population area may appear specifically and stably in the scattergram formed by plotting forward-scattered light intensity against side-scattered light intensity. This cell population can be identified as red blood cells infected by plasmodium.

Figure 1:
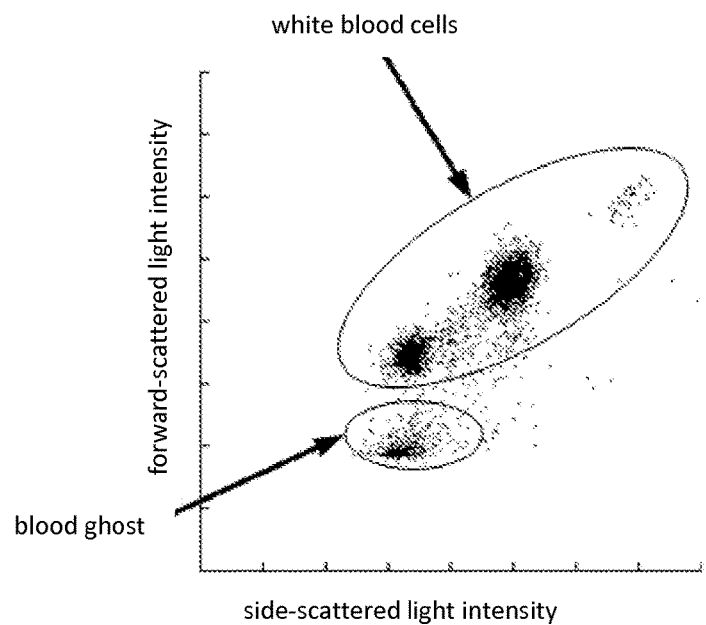
FIG. 1 is a scattergram formed by plotting forward-scattered light intensity against side-scattered light intensity of a normal blood sample in accordance with an embodiment of the present disclosure.
Figure 2:
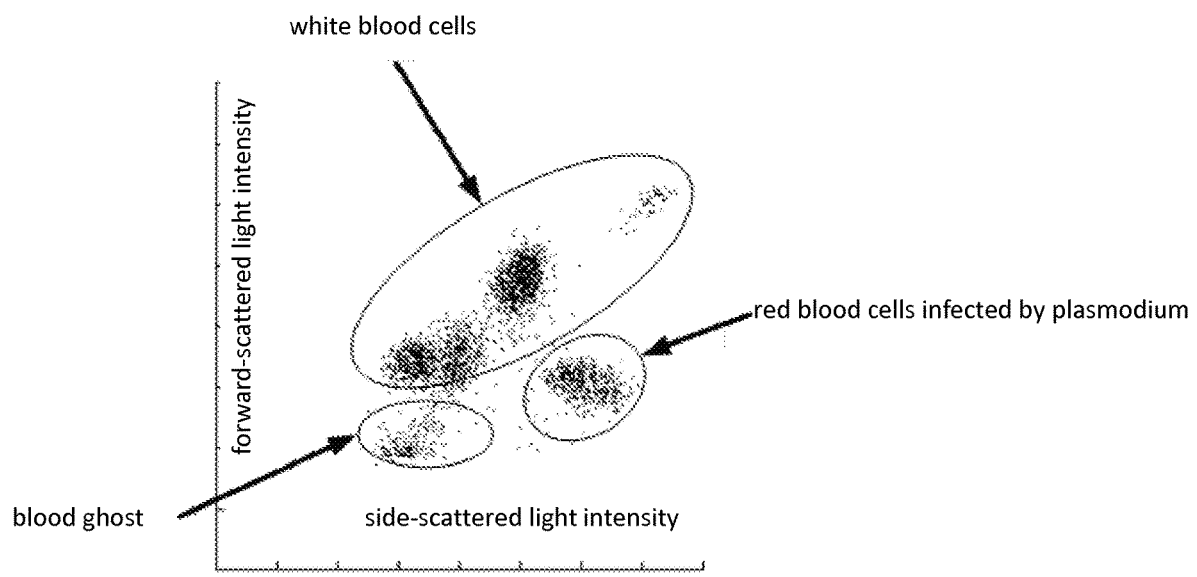
FIG. 2 is a scattergram formed by plotting forward-scattered light intensity against side-scattered light intensity of a blood sample infected by plasmodium in accordance with an embodiment of the present disclosure.

For convenience of explanation, a scattergram formed by plotting forward-scattered light intensity against side-scattered light intensity for a normal blood sample is provided in FIG. 1, while a scattergram formed by plotting forward-scattered light intensity against side-scattered light intensity for a blood sample infected by plasmodium is provided in FIG. 2. By comparing FIG. 1 and FIG. 2, a specific area representing cells infected by plasmodium can be seen in FIG. 2.

Moreover, it has been found through experiments that red blood cells infected by plasmodium may have lower average fluorescence intensity than normal white blood cells, so there might be a cell population area under the normal white blood cells area in the three-dimensional scattergram classifying white blood cells (X-axis is side-scattered light intensity, Y-axis is forward-scattered light intensity and Z-axis is fluorescence intensity). After experiments, a cell population area does exist clearly in the assumed area of the three-dimensional scattergram of white blood cells classification. This may be shown by comparing FIG. 8 and FIG. 9, where a specific area representing cells infected by plasmodium can be seen in FIG. 8.

Figure 3:
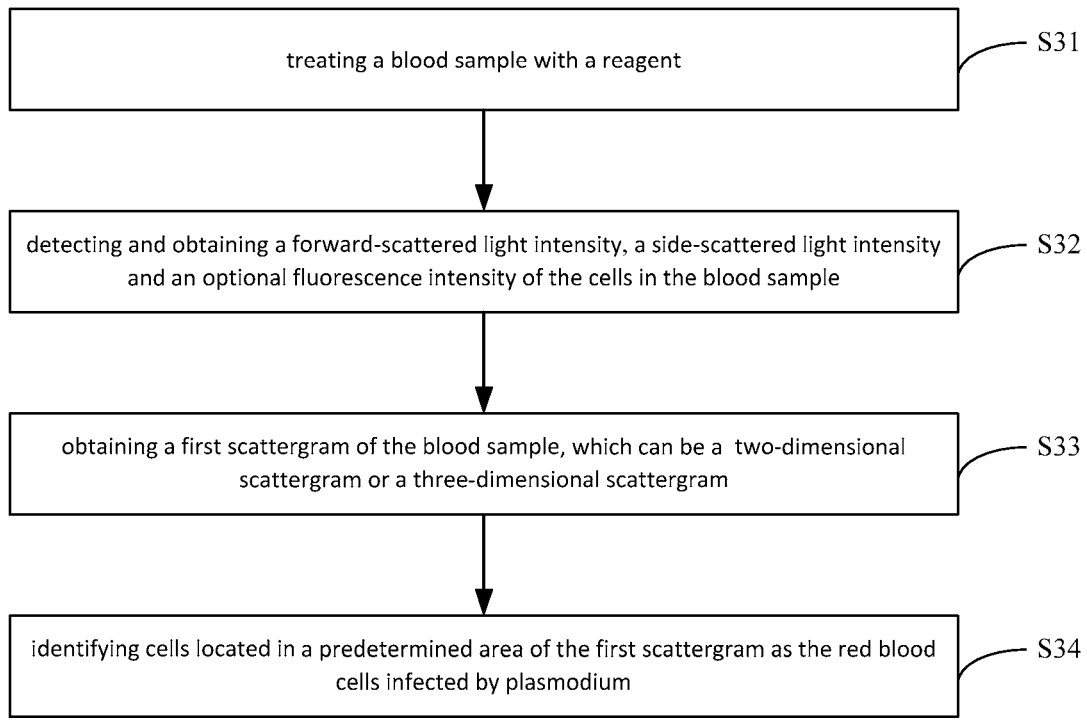
FIG. 3 is a flow diagram which shows a method for identifying red blood cells infected by plasmodium in accordance with an embodiment of the present disclosure.
Figure 4:
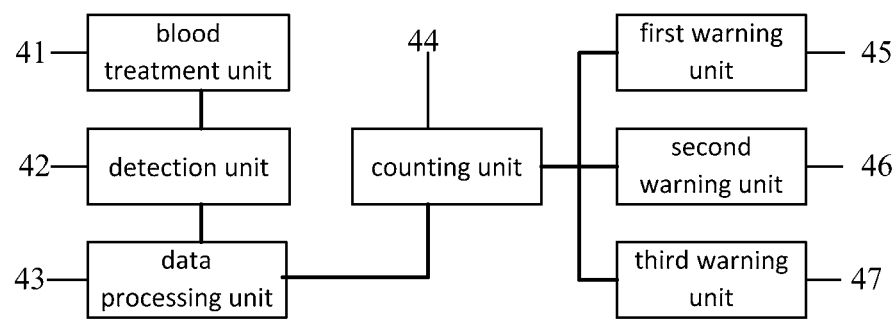
FIG. 4 is a block diagram which shows an apparatus for identifying red blood cells infected by plasmodium in accordance with an embodiment of the present disclosure.

In one embodiment, a method for identifying red blood cells infected by plasmodium is provided that can be performed a flow cytometer. The method is shown in FIG. 3, which may include:

S31, treating a blood sample with a reagent;

S32, detecting and obtaining a forward-scattered light intensity, a side-scattered light intensity and an optional fluorescence intensity of cells in the treated blood sample;

S33, obtaining a first scattergram of the blood sample, which can be a two-dimensional scattergram or a three-dimensional scattergram; and S34, identifying cells located in a predetermined area of the first scattergram as the red blood cells infected by plasmodium.

In this embodiment, the blood sample may be treated and analyzed with a flow cytometry to obtain a scattergram, and then the red blood cells infected by plasmodium be identified according to cell areas of the scattergram. Since the method can be performed with an automatic analyzer, it may have less anthropic factor, better accuracy and fast test speed. Moreover, all the cells in the blood sample would be tested, so the number of the cells tested would be higher than that of the conventional method using a microscope. The accuracy of the method described herein may be further improved, because missed diagnosis, which can be caused by an insufficient number of red blood cells being checked under the microscope, would be less likely to occur.

It should be noted that the reagent used in S31 can be a hemolytic agent. The hemolytic agent should not be limited to any specific component. A reagent may be feasible so long as it can lyse normal red blood cells. For example, the reagent may include a fluorescent dye for labeling cells and a surfactant for partly lysing membranes of white blood cells. In one embodiment, the surfactant can be a cationic surfactant, for example, a quaternary ammonium salt. In addition, there is no special limit to the mixing ratio of a blood sample and a hemolytic agent, for example, the ratio can be 1:50 or 1:45, so long as normal red blood cells may be lysed.

The fluorescence intensity can be optionally detected and obtained in S32, based on user's need. When the fluorescence intensity is used in the method, a three-dimensional scattergram can be obtained according to the forward-scattered light intensity, the side-scattered light intensity and the fluorescence intensity after the blood sample is treated and analyzed by the flow cytometer. In S32, the three-dimensional scattergram obtained from the three light signals may provide better identification accuracy of red blood cells infected by plasmodium, as compared to the two-dimensional scattergram obtained from the forward-scattered light intensity and the side-scattered light intensity only.

In one embodiment, the method further comprises: counting number of red blood cells infected by plasmodium, obtaining a blood routine examination parameter of erythrocytic series which correlate with plasmodium infection in the blood sample, and giving a warning signal if the number is more than a second threshold value and the blood routine examination parameter of erythrocytic series which correlates with plasmodium is out of its normal range.

In one embodiment, after S34, the method can further include: counting a number of the red blood cells infected by plasmodium in the scattergram, and giving a warning signal if the number is more than a first threshold value. The warning signal can be given by combining with other conditions. Since plasmodium infection can cause more than one blood routine examination parameter of erythrocytic series which correlates with plasmodium to exceed its normal range, after combining with the cell counting result, the warning signal may be given when there is a lower number of red blood cells infected by plasmodium (e.g., where the second threshold value is lower than the first threshold value), thereby improving identification sensitivity. The blood routine examination parameter of erythrocytic series which correlates with plasmodium infection can be selected from Red Blood Cell count (RBC), Hemoglobin Concentration (HGB), Mean Corpuscular Hemoglobin (MCH), Mean Corpuscular Hemoglobin Concentration (MCHC), Mean Corpuscular Volume (MCV) and Hematocrit (HCT). It should be noted that the threshold value may be a definite value or a ratio, for example, the ratio of the number of red blood cells to that of total blood cells.

In one embodiment, after S34, the method may further include counting a number of the red blood cells infected by plasmodium; obtaining a second scattergram when the number is more than a third threshold value; giving a warning signal when there is abnormal information in the second scattergram.

The second scattergram may be a scattergram formed by plotting side-scattered light intensity against fluorescence intensity. The abnormal information can be related to red blood cells infected by plasmodium. For example, if a cell population having higher fluorescence intensity appears in the second scattergram, it may be considered that there is abnormal information in the second scattergram. Cell population having higher fluorescence intensity appears means that the fluorescence signals with higher intensity could be recognized as cell population after signals processing. For example, in some cases, a cell population having higher fluorescence can appear above the area of monocytes and lymphocytes in the second scattergram.

In one embodiment, an apparatus for identifying red blood cells infected by plasmodium is provided that can include:

a blood treatment unit 41, which treats a blood sample to obtain a treated sample;

a detection unit 42, which detects the treated sample and obtains scattered light signals; and a data processing unit 43, which obtains a scattergram according to the scattered light signals, and identifies cells located in a predetermined area of the scattergram as the red blood cells infected by plasmodium.

With this apparatus, a blood sample can be treated with a reagent, and then detected to obtain a scattergram by flow cytometry. Red blood cells infected by plasmodium may be identified according to cell areas of the scattergram. The apparatus are performed with an automatic analyzer, so people's influence may be reduced and the apparatus can have faster detection speed and higher identification accuracy. Moreover, since all the cells in a blood sample may be analyzed with the apparatus and the number of the cells detected can be relatively high, missed diagnosis caused by an insufficient number of blood cells inspected would likely not occur, thereby improving identification accuracy.

In some implementations, the detection unit 42 can further obtain fluorescence signals of cells in the treated sample.

In another embodiment, the apparatus may further include:

a counting unit 44, which counts a number of the red blood cells infected by plasmodium; and a first warning unit 45, which gives a warning signal if the number is more than a first threshold value.

In still another embodiment, the data processing unit 43 can further obtain a blood routine examination parameter of erythrocytic series which correlates with plasmodium, and the apparatus can further include:

a counting unit 44, which counts a number of the red blood cells infected by plasmodium; and a second warning unit 46, which gives a warning signal if the number is more than a second threshold value and the parameter is out of its normal range.

The meanings of the threshold value and the blood routine examination parameter of erythrocytic series are the same as those for the method embodiments described above.

In some cases, the blood routine examination parameter of erythrocytic series which correlates with plasmodium can be the total number of red blood cells or the hemoglobin concentration.

In yet another embodiment, the apparatus may further include:

a counting unit 44, which counts a number of the red blood cells infected by plasmodium;

a third warning unit 47, which obtains a second scattergram when the number is more than a third threshold value; and gives a warning signal when a cell population having higher fluorescence intensity appears in the second scattergram; where the second scattergram is formed by plotting side-scattered light intensity against fluorescence intensity of the blood sample.

In the apparatus embodiments described above, the blood sample can be treated with the same reagent as the method embodiments described above.

Figure 5:
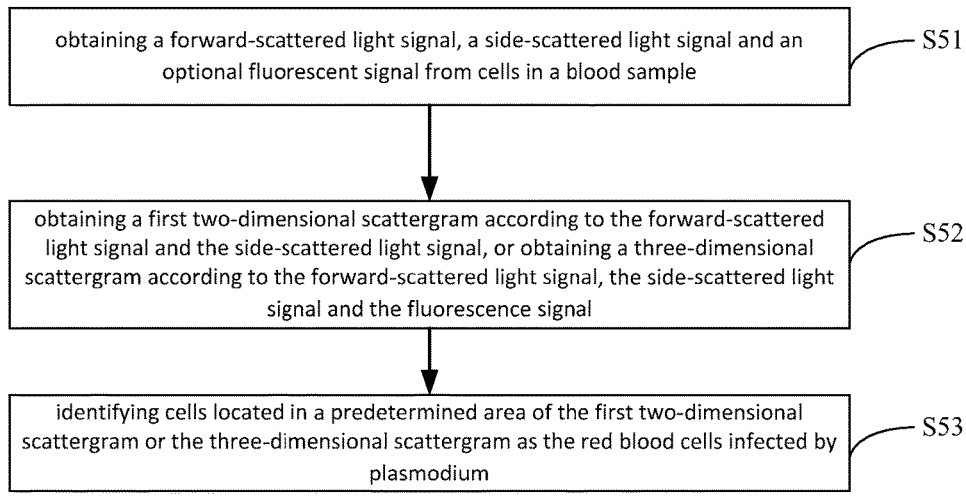
FIG. 5 is a flow diagram which shows a method for identifying red blood cells infected by plasmodium in accordance with another embodiment of the present disclosure.

As shown in FIG. 5, a method for identifying red blood cells infected by plasmodium is provided that may include:

S51, obtaining a forward-scattered light signal, a side-scattered light signal and an optional fluorescence signal from cells in a blood sample;

S52, obtaining a first two-dimensional scattergram according to the forward-scattered light signal and the side-scattered light signal, or obtaining a three-dimensional scattergram according to the forward-scattered light signal, the side-scattered light signal and the fluorescence signal; and S53, identifying cells located in a predetermined area of the first two-dimensional scattergram or the three-dimensional scattergram as the red blood cells infected by plasmodium.

This method can acquire a forward-scattered light signal, a side-scattered light signal and an optional fluorescence signal from cells in a blood sample so as to obtain a first two-dimensional scattergram or a three-dimensional scattergram. Red blood cells infected by plasmodium may be identified according to the scattergram. The method may be performed by an automatic analyzer, so it can have less anthropic factor, better accuracy and fast test speed.

In one embodiment, after S53, the method further comprises:

counting number of red blood cells infected by plasmodium, and giving a warning signal if the number is more than a first threshold value.

In another embodiment, after S53, the method may further include:

counting a number of the red blood cells infected by plasmodium; obtaining a blood routine examination parameter of erythrocytic series which correlates with plasmodium infection in the blood sample; and giving a warning signal if the number is more than a second threshold value and the blood routine examination parameter of erythrocytic series is out of its normal range. In some implementations, the blood routine examination parameter of erythrocytic series which correlates with plasmodium infection can be the total number of red blood cells or the hemoglobin concentration.

In another embodiment, after S53, the method can further include:

counting a number of the red blood cells infected by plasmodium; obtaining a second two-dimensional scattergram according to the side-scattered light signal and the fluorescence signal; and giving a warning signal if a cell population having higher fluorescence intensity appears in the second two-dimensional scattergram and the number is more than a third threshold value.

The meanings of the threshold value and the cell population having higher fluorescence intensity are the same as those for the method embodiments described above.

Figure 6:
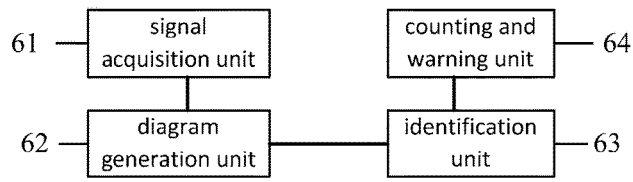
FIG. 6 is a block diagram which shows an apparatus for identifying red blood cells infected by plasmodium in accordance with another embodiment of the present disclosure.

As shown in FIG. 6, an apparatus for identifying red blood cells infected by plasmodium is provided that may include:

a signal acquisition unit 61, which obtains a forward-scattered light signal, a side-scattered light signal and an optional fluorescence signal from cells in a blood sample;

a diagram generation unit 62, which obtains a first two-dimensional scattergram according to the forward-scattered light signal and the side-scattered light signal, or obtains a three-dimensional scattergram according to the forward-scattered light signal, the side-scattered light signal the fluorescence signal; and an identification unit 63, which identifies cells located in a predetermined area of the first two-dimensional scattergram or the three-dimensional scattergram as the red blood cells infected by plasmodium.

This apparatus can acquire a forward-scattered light signal, a side-scattered light signal and an optional fluorescence signal from cells in a blood sample so as to obtain a first two-dimensional scattergram or a three-dimensional scattergram, and then identify cells located in a predetermined area as the red blood cells infected by plasmodium. The apparatus could be performed by an automatic analyzer, so it may have better test accuracy and faster test speed due to less anthropic factor.

In one embodiment, the apparatus can further include:

a counting and warning unit 64, which counts a number of the red blood cells infected by plasmodium; and gives a warning signal if the number is more than a first threshold value.

In another embodiment, the apparatus can further include:

a counting and warning unit 64, which counts a number of the red blood cells infected by plasmodium and acquires a blood routine examination parameter of erythrocytic series which correlates with plasmodium, and gives a warning signal if the number is more than a second threshold value and the parameter is out of its normal range.

In still another embodiment, the apparatus can further include:

a counting and warning unit 64, which counts a number of the red blood cells infected by plasmodium and obtains a second two-dimensional scattergram according to the side-scattered light signal and the fluorescence signal of the blood sample, and gives a warning signal if a cell population having higher fluorescence intensity appears in the second two-dimensional scattergram and the number is more than a third threshold value.

In the present disclosure, the predetermined area can be specific area in the scattergrams which can be obtained by statistically comparing the scattergrams of normal blood samples and malaria patients' blood samples. The parameter of the specific area may be inputted into the identification unit so as to obtain the predetermined area. In a scattergram of an unknown sample, cells in the predetermined area can be identified as the red blood cells infected by plasmodium.

Alternatively, the predetermined area may be defined according to a function describing the relative location between normal white blood cells area and infected red blood cells area. This function can be obtained by statistically comparing the scattergrams of normal blood samples and malaria patients' blood samples, such as, calculating function of area location of red blood cells infected by plasmodium and that of normal white blood cells. Then the function relation can be inputted into the identification unit. In a scattergram of an unknown sample, the predetermined area may be determined according to the location of normal white blood cells area and that function.

In the present disclosure, the first, second and third threshold values can be the number of red blood cells infected by plasmodium, or alternatively the percentage of red blood cells infected by plasmodium as compared to normal red blood cells. The second and the third threshold values may be the same value or different value, base on user's need. The threshold values may be predetermined or inputted by user through an interactive interface.

EXAMPLE 1

Figure 7:
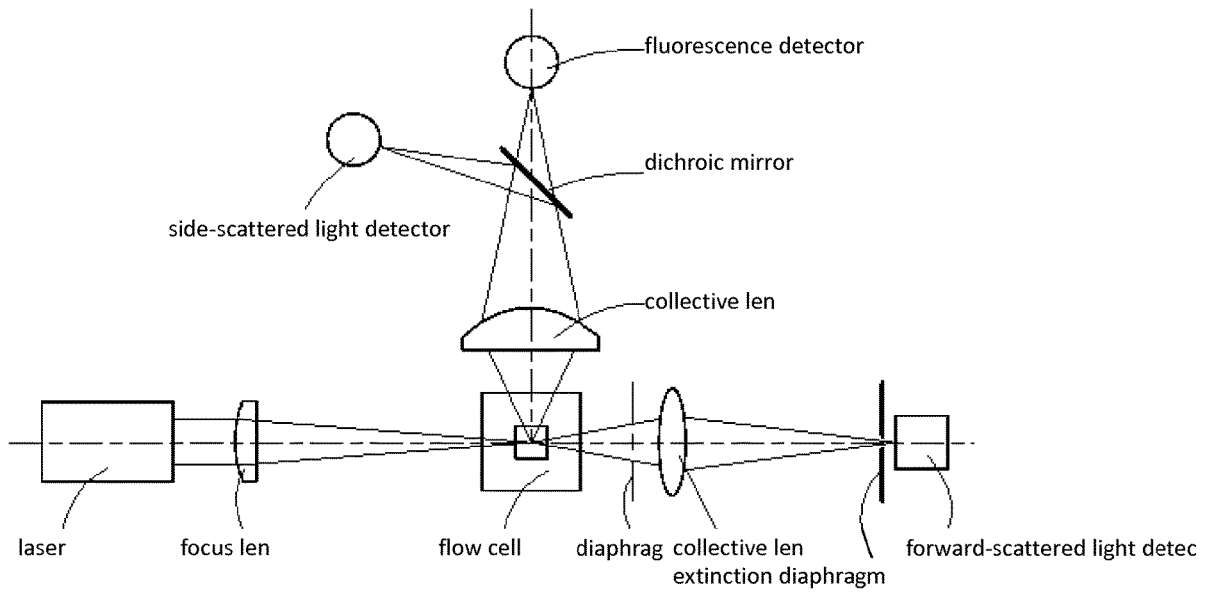
FIG. 7 is schematic representation of a flow cytometer in Example 1.

This Example provides an example method for identifying red blood cells infected by plasmodium according to the present disclosure. The method was performed by a flow cytometer, such as BC series flow cytometer manufactured by Shenzhen Mindray Bio-Medical Electronics Co. Ltd (Shenzhen, People's Republic of China), whose schematic representation is shown in FIG. 7.

A malaria patient's blood sample was treated by a reagent, which included Reagent A having following components:

| | |
|---|---|
| Dye A | 0.5 ppm |
| decylisoquinolinium bromide | 0.4 g/L |
| polyoxyethylene (23) lauryl ether | 1.3 g/L |
| sodium benzoate | 2.0 g/L |
| methanol | 50 g/L |
| monobasic sodium phosphate | 3 g/L |
| dibasic sodium phosphate | 4.8 g/L | where the structure of dye A was

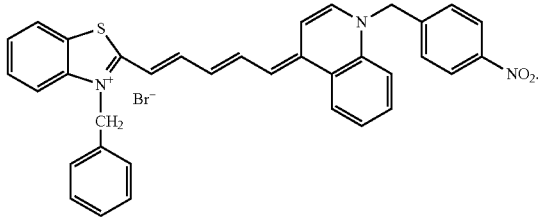 [SMILES: O=[N+]([O-])c1ccc(CN2C=C\C(=C/C=C/C=C/c3sc4ccccc4[n+]3Cc3ccccc3)c3ccccc32)cc1 ; [Br-]]

1ml of the reagent was mixed with 20 ul of the blood sample.

Figure 8:
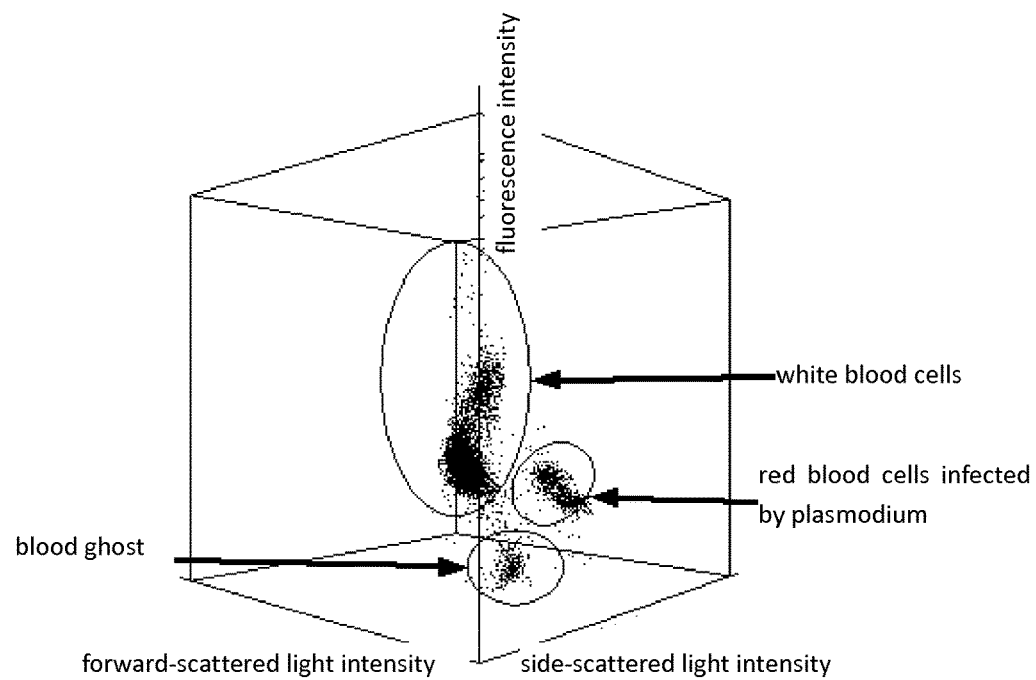
FIG. 8 is a three-dimensional scattergram for a blood sample infected by plasmodium in Example 1.
Figure 9:
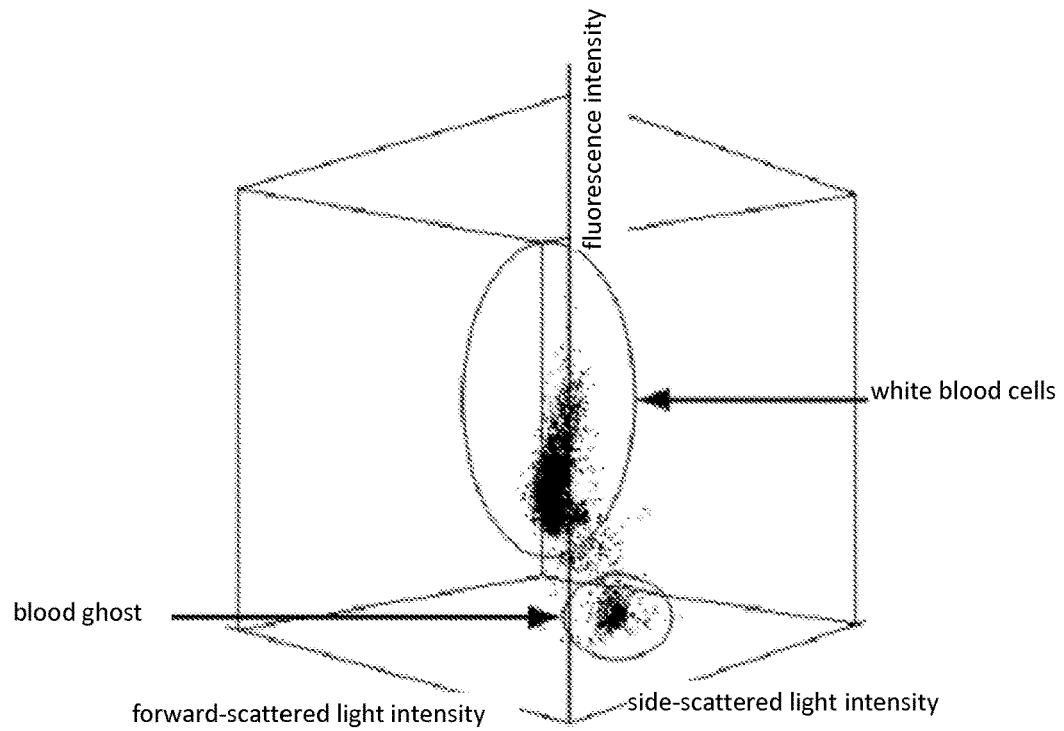
FIG. 9 is a three-dimensional scattergram for a normal blood sample in Example 1.
Figure 10:
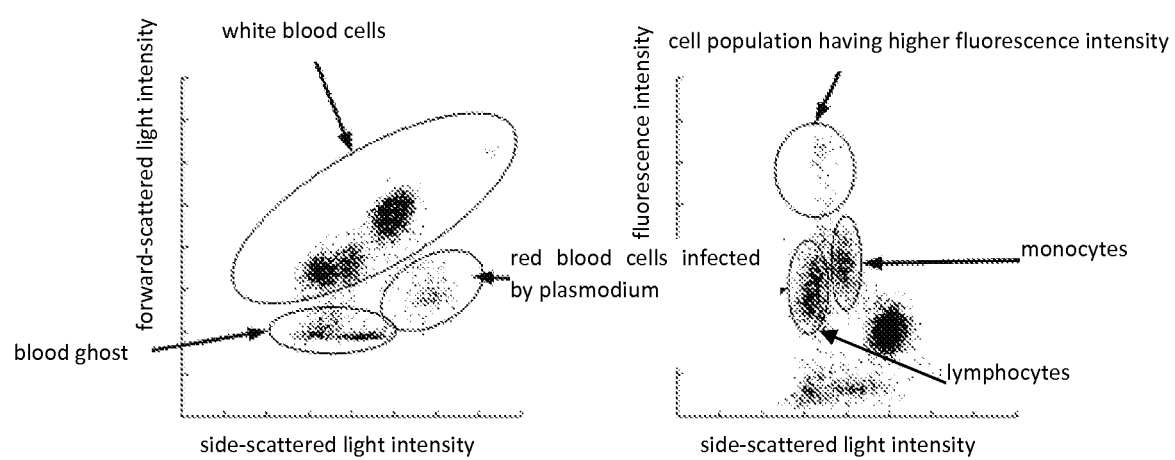
FIG. 10 shows two two-dimensional scattergrams in Example 1.

After the blood sample was treated with the reagent, side fluorescence at a detection angle of 90° was used to measure fluorescence intensity of treated cells, side-scattered light at a detection angle of 90° was used to measure side-scattered light intensity of treated cells, and forward-scattered light at a detection angle of 2°-5° was used to measure forward-scattered light intensity. A three-dimensional scattergram of the blood sample, which is shown in FIG. 8, was then obtained according to these three intensities. Cells located in a predetermined area of FIG. 8 were identified as red blood cells infected by plasmodium.

Since the number of red blood cells infected by plasmodium was more than a first threshold value, a warning signal was given. Alternatively, the number was less than the first threshold value, but was more than a second threshold value, and the total number of red blood cells or hemoglobin concentration was less than the normal value, a warning signal was given. Alternatively, a warning signal was given, the number of red blood cells infected by plasmodium in a first two-dimensional scattergram, which was formed by plotting the forward scattered light intensity against the side-scattered light intensity (shown in FIG. 10), was more than the second threshold value, and a cell population having higher fluorescence intensity appeared above the area of monocytes and lymphocytes in a second two-dimensional scattergram, which was formed by plotting the side-scattered light intensity against the fluorescence intensity (shown in FIG. 10). Since malaria pigments can be taken by some white blood cells in a malaria patient's blood sample, a cell population having higher fluorescence intensity than normal white blood cells may appear in the scattergram (shown in the left scattergram of FIG. 10).

It is noted that other reagents for white blood cells classification also can be used in the present disclosure. For example, the reagent may be those disclosed in US20110027788. The reagent can include:

(1) cationic cyanine compounds selected from those having the following general formulae I and II:

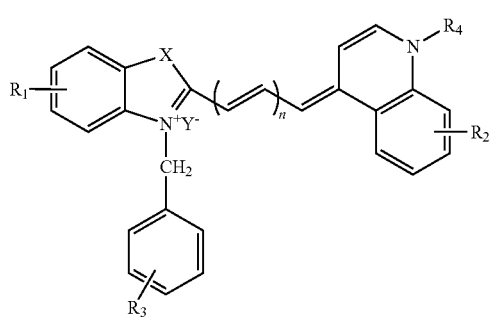

where
n is 1, 2 or 3;
X is $C(CH_3)_2$, O, S or Se;
$R_1$ and $R_2$ are each independently selected from H, $C_{1-18}$alkyl, —$C_{1-6}$alkyl-$OR_5$ or a halogen;
$R_3$ is H, $C_{1-18}$alkyl, $OR_5$, —$C_{1-6}$alkyl-$OR_5$, $COOR_5$, $NO_2$, CN or a halogen;
$R_4$ is $C_{1-18}$alkyl, —$C_{1-6}$alkyl-$OR_5$, benzyl or a halogen, where the benzyl can be optionally substituted with a substituent selected from a halogen, hydroxyl, sulfhydryl, cyano, nitro, alkyl, aryl, alkyloxy, heterocyclyl, haloalkyl, amino, alkylamino, amido or carboxyl;
$R_5$ is H or $C_{1-18}$alkyl; and
$Y^-$ is an anion;
or

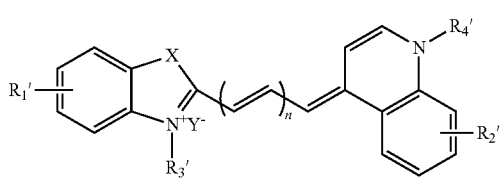

where
n is 1, 2 or 3;
X is $C(CH_3)_2$, O, S or Se;
R1' and R2' are each independently selected from H, OH, C1-18alkyl, C1-6alkylOR5', C1-18alkylsulfonyl, phenyl or a halogen;
$R_3'$ and $R_4'$ are each independently selected from $C_{1-18}$alkylCOOR$_6$', $C_{1-18}$alkylOR$_6$' or benzyl, where the benzyl can be optionally substituted with a substituent selected from a halogen, hydroxyl, sulfhydryl, cyano, nitro, alkyl, aryl, alkyloxy, heterocyclyl, haloalkyl, amino, alkylamino, amido or carboxyl, provided that $R_3'$ and $R_4'$ are not simultaneously benzyl, and $R_4'$ is not $C_{1-18}$alkylOR$_6$' when $R_3'$ is benzyl;
$R_5'$ is $C_{1-18}$alkyl or H;
$R_6'$ is $C_{1-18}$alkyl, H or phenyl, where the phenyl can be optionally substituted with a substituent selected from a halogen, hydroxyl, sulfhydryl, cyano, nitro, alkyl, aryl, alkyloxy, heterocyclyl, haloalkyl, amino, alkylamino, amido or carboxyl; and
Y— is an anion;

(2) cationic surfactants that are quinolinium salt-type cationic surfactants having the following general formulae III and/or IV:

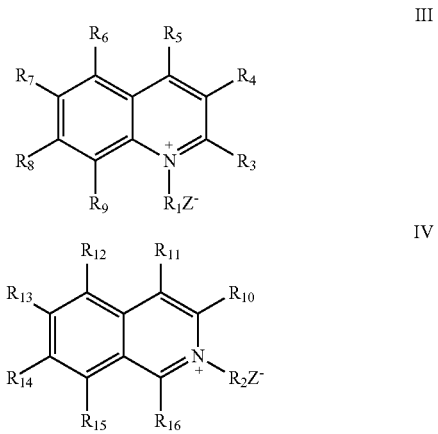

where
$R_1$ and $R_2$ are each independently selected from $C_{6-18}$alkyl and $C_{6-18}$haloalkyl;
$R_3$ to $R_{16}$ are each independently selected from H, OH, $C_{1-4}$alkyl, $C_{1-4}$alkyloxy and sulphonyl; and
$Z^-$ is a halogen ion;
and/or
quaternary ammonium salt-type cationic surfactants having the following general formula V:

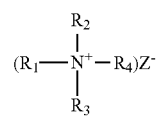

where
$R_1$ is $C_{6-14}$alkyl or $C_{6-14}$alkenyl, and in one embodiment straight alkyls such as hexyl, octyl, decyl, lauryl or myristyl, and in another embodiment straight alkyls such as octyl, decyl, lauryl or myristyl;

$R_2$ is $C_{1-4}$alkyl or $C_{2-4}$alkenyl, for example, in one embodiment methyl, ethyl, propyl, butyl or butenyl, and in another embodiment methyl, ethyl or propyl;

$R_3$ is $C_{1-4}$alkyl or $C_{2-4}$alkenyl, for example, in one embodiment methyl, ethyl, propyl, butyl or butenyl, and in another embodiment methyl, ethyl or propyl;

$R_4$ is $C_{1-4}$alkyl, $C_{2-4}$alkenyl or benzyl, for example, in one embodiment methyl, ethyl, propyl, butyl, butenyl or benzyl, and in another embodiment methyl, ethyl or propyl;

$Z^-$ is a halogen ion;

(3) at least one nonionic surfactant.

The reagent further can include at least one anionic compound selected from those having one or more carboxyl or sulphonyl groups.

The aforesaid compounds having the general formula I can be:

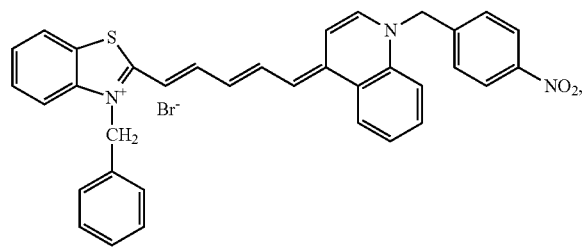

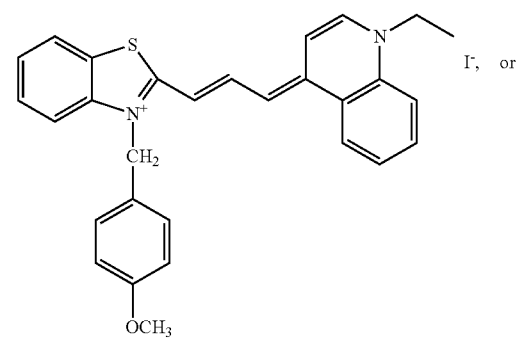

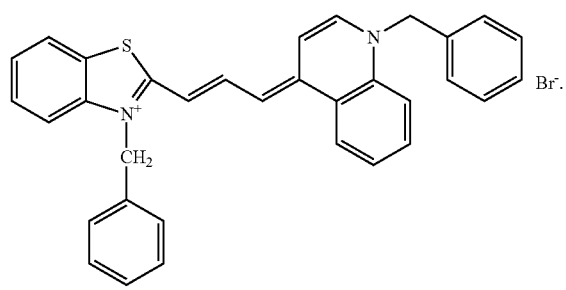

The aforesaid compounds having the general formula II can be:

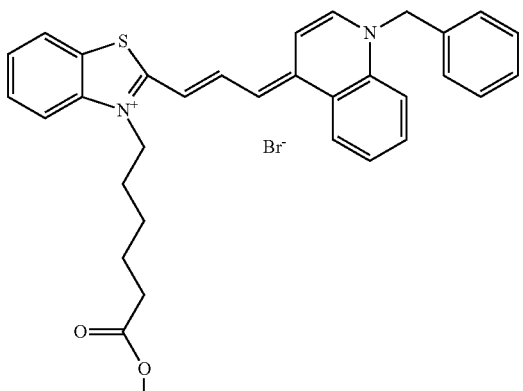

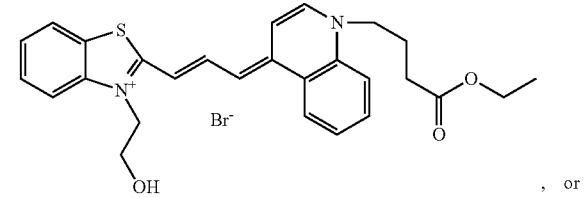

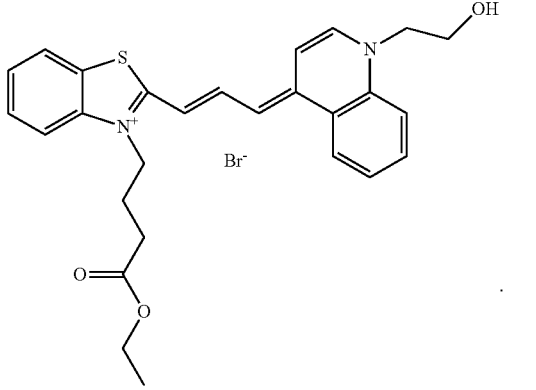

The detailed components and preparation of the reagent also are disclosed in US20110027788.

A skilled artisan will understand that the apparatuses and methods described herein can be achieved by electronic hardware, or by a combination of computer software and electronic hardware. Whether the functions should be performed through hardware or software may depend on particular applications and design constraints. Skilled artisan can use different methods to implement the functions described according to different applications. However, such implementations shall be deemed to be within the scope of the present disclosure.

As will be appreciated by one of ordinary skill in the art, specific implementations of the systems, apparatuses and components described herein may be developed with reference to the various embodiments described above.

It shall be understood that the apparatuses and methods described in the present disclosure may be achieved by other ways. For example, the apparatus examples are exemplary embodiments. The units can be divided based on logic functions or some other ways, such as multiple units or components may be combined or integrated into another system, or certain features may be ignored or not executed.

Units described as separate components may or may not be physically separated. Components described as units may or may not be physical units, that is the components may be located in one place or distributed as multiple network units. Some or all units can be selected based on practical need so as to achieve the purpose of the present disclosure.

Additionally, function units of the present disclosure may be integrated into a single processor, or each unit may separately physically exist, or two or more units may be integrated into one unit.

If the above-described functions are performed by software function units and sold or used as an independent product, they may be stored in a computer-readable memory. Based on this understanding, substance of the present disclosure, contribution with respect to prior art, or part of technical solution may be provided as computer program. The computer program, which may be stored in a memory, can include instructions that direct a computer such as personal computer, server, or network devices to execute some or all steps of the exemplary methods. The memory may be flash memory, mobile hard disk, read-only memory, random access memory, hard disks or optical storage devices (CD-ROMs, DVDs, Blu-Ray discs, and the like), or other medium that can store program codes.

This disclosure has been made with reference to various exemplary embodiments including the best mode. These and other changes or modifications are intended to be included within the scope of the present disclosure.

The invention claimed is:

1. A method for identifying red blood cells infected by plasmodium while classifying white blood cells in a blood sample, said method comprising:
    treating the blood sample with a reagent comprising a hemolytic agent for lysing normal red blood cells, wherein the normal red blood cells are lysed into erythrocyte ghosts;
    transmitting light into the blood sample;
    detecting from within the blood sample a forward-scattered light intensity, a side-scattered light intensity and a fluorescence intensity from cells in the blood sample;
    obtaining a three-dimensional scattergram generated from a combination of the forward-scattered light intensity, the side-scattered light intensity and the fluorescence intensity;
    identifying cells located in a defined area of the three-dimensional scattergram as the red blood cells infected by plasmodium, wherein the cells located in the defined area are separated from an area where the erythrocyte ghosts are located, and wherein the defined area is determined according to a location of normal white blood cells and a function describing the relative location between an area of normal white blood cells and an area of red blood cells infected by plasmodium;
    counting the number of the red blood cells infected by plasmodium in the defined area;
    obtaining a blood routine examination parameter of erythrocytic series which correlates with plasmodium of the blood sample; and
    giving a warning signal when the number of the red blood cells infected by plasmodium is more than a first threshold value or when the number of the red blood cells infected by plasmodium is less than the first threshold value and more than a second threshold value, and the blood routine examination parameter of erythrocytic series is out of a normal range.

2. The method according to claim 1, wherein the blood routine examination parameter of erythrocytic series which correlates with plasmodium is selected from red blood cell count, hemoglobin concentration, mean corpuscular hemoglobin, mean corpuscular hemoglobin concentration, mean corpuscular volume, or hematocrit.

3. The method according to claim 1, said method further comprising:
    giving a warning signal when a cell population having higher fluorescence intensity than lymphocytes appears in the three-dimensional scattergram, the blood routine examination parameter is out of a normal range, and the number of cells in the defined area is more than a third threshold value.

* * * * *